United States Patent [19]

Feldon et al.

[11] Patent Number: 4,597,648
[45] Date of Patent: Jul. 1, 1986

[54] KERATOMETER

[75] Inventors: Steven E. Feldon, San Marino; Barry G. Broome, Glendora; David A. Wallace, Hermosa Beach, all of Calif.

[73] Assignee: Keratometer Research and Development, Hermosa Beach, Calif.

[21] Appl. No.: 481,286

[22] Filed: Apr. 1, 1983

[51] Int. Cl.⁴ ............................................... A61B 3/10
[52] U.S. Cl. .................................... 351/212; 351/205; 351/221
[58] Field of Search ............... 351/205, 210, 211, 212, 351/214, 221

[56] References Cited

U.S. PATENT DOCUMENTS 4,157,859  6/1979  Terry ................................... 351/212
4,429,960  2/1984  Mocilac et al. ...................... 351/212

OTHER PUBLICATIONS

Troutman et al., The Use and Preliminary Results of the Troutman Surgical Keratometer in Cataract and Corneal Surgery, vol. 83, Apr. 1977, Transcripts Amer. Acd. of Opth. & Otol.
Halberg et al., A New Autokeratometer, vol. 8, No. 3, Contact Lens, Sep. 1982.
Smirmaul, The Smirmaul Quantitative Surgical Keratometer, Feb. 1983.

Primary Examiner—Rodney B. Bovernick
Assistant Examiner—P. Dzicozynski
Attorney, Agent, or Firm—Price, Gess & Ubell

[57] ABSTRACT

An improved keratometer instrument capable of measuring keratometric values of an eye is provided. An optical reference of a predetermined dimensional value is directed at the cornea of the eye and an optical sensor measures the same at different meridians. A computer circuit can determine whether the instrument is de-centered or de-focused relative to the eye and can derive measurements of keratometric values. The axis of astigmatism can be visually displayed to the surgeon during an operation.

16 Claims, 7 Drawing Figures

KERATOMETER

BACKGROUND OF THE INVENTION

1. Field of the Invention

The present invention relates to an instrument for keratometry, and more specifically, to an improved keratometer that is capable of quantitatively measuring keratometric values for human eyes.

2. Description of the Prior Art

The prior art is aware of several types of medical instruments that have been developed to allow a medical examiner to obtain information about corneal curvature, surface regularities and dioptric refractive power of the cornea undergoing examination. A keratoscope is a type of medical instrument that gives qualitative information about corneal topography and curvature by allowing the medical examiner to observe the corneal reflection pattern produced by an object or objects of known geometric dimensions that are incorporated into and illuminated by the instrument. A keratometer differs from a keratoscope in that it provides quantitative measurement of corneal curvature, usually expressed as dioptric refractive power, as well as providing qualitative information about corneal topography.

In the prior art, keratometer devices have generally been derived from a single generic design, attributed to Helmholtz, that infers corneal power by measuring the image magnification of a known object geometry produced by corneal reflection utilizing the separation between two or more images of the object. Instruments of this type incorporate an illuminated mire image which is projected onto the cornea under examination. The reflected images are viewed by the examiner through an optical system aligned coaxially with the cornea. The optical system can incorporate a system of image doubling, through use of a bi-prism, risley prisms, or other optical construction, that causes formation of one or more secondary images displaced from the primary image. The amount of displacement can be adjusted mechanically or optically, and when brought into adjustment either by superimposition of mires, or tangency of mires, an indirect measurement of image size is inferred. The size of the reflected corneal image is proportional to corneal curvature and if the mire dimensions, optical system geometry, and image size are known, the curvature of the cornea can be quantitatively inferred.

Recently, keratometers have been used during eye surgery to allow the surgeon to monitor and eliminate any undesired astigmatism through modification of wound closure at the time of the surgery.

A "surgical" keratometer is a type of keratometer device that attaches to or modifies an operating microscope, allowing the surgeon to observe corneal topography and in some instances measure corneal curvature intraoperatively, on an eye undergoing surgery. This measurement is of value in that wound closure and suture tension can be modified, based upon the keratometric measurements, so as to minimize any undesired astigmatism induced by the operative procedure.

A surgical keratometer differs from a clinical keratometer in that it is designed to allow the observer (surgeon) to view the reflection of the keratometric mires through the surgical microscope optical system as he is viewing the surgical field. Furthermore, the eye under examination is anesthetised, through either general or local retrobulbar anesthesia of the patient.

The first device to be developed in this category was the Troutman Surgical Keratometer, which should actually be classified as a type of keratoscope (and not a type of keratometer) because it only provides for viewing of a number of light sources arranged in a circular pattern around the entrance pupil of the microscope, and is not capable of precise quantitative measurements of corneal curvature.

The Smirmaul Surgical Keratometer is a semiquantitative device, in that it does incorporate image-doubling of an object mire, and allows positional adjustment of the doubled image. When properly adjusted, inference can be made regarding corneal dioptric power. Because it cannot be accurately and reproducibly calibrated, however, its measurements of corneal dioptric power are prone to inaccuracy. It is somewhat useful in determining axis and power of corneal astigmatism, since this is a relative determination based upon the arithmetic difference between the values obtained for maximum and minimum curvature.

The Terry Keratometer is a surgical keratometer capable of quantitative measurement of corneal curvature. It incorporates an illuminated circular object mire placed immediately below the entrance pupil of the microscope, and a series of image-doubling prisms installed inside the housing of the microscope. The surgeon mechanically adjusts the prisms to merge two or more Purkinje images of the mire that appear to be located behind the corneal surface. This method indirectly measures the Purkinje image diameter by displacement of the doubled Purkinje images. Because it can be accurately calibrated, the instrument is capable of yielding reliable data. However, installing the Terry device requires mechanical alteration of the microscope, and electronic interfacing with the control circuitry for the microscope zoom function, both of which pose theoretical and practical objections to its design.

Finally, the Humphrey Auto Keratometer is a type of instrument that utilizes three rays of infrared light which are directly reflected off of the corneal surface to three separate photodetectors whose spatial geometry allows inference of corneal curvature in two orthogonal meridians. A chopper disc provides means for determining which infrared ray is received by each of the photodetectors.

These types of instrument design have several useful characteristics. First, the direct measurement of the size of a corneal reflected image in the past has been quite difficult, whereas the indirect method employed above was easy and optically simple. Second, the technique can be employed in the presence of microscopic oscillations and movements of the eye which are present in the awake individual, even while the subject is attempting steady fixation.

There is significant disadvantage to the use of image-doubling prisms in keratometer design, especially relevant to intraoperative use of a surgical keratometer. In this setting, the surgeon desires to view the operative field concurrent with the mires necessary to measure keratometry. With any image-doubling optical scheme, there will be doubling of not only the keratometry mires, but also of objects within the surgical field, creating a ghost image clearly visible to the surgeon. Also, because of the nature of image doubling prisms, some image-smear is usually created by the prisms which cause slight degradation of even the primary image.

Both of these types of image degradations are undesirable to the surgeon.

The greatest disadvantage of the above keratometers is the fact that the surgeon must physically intervene to adjust the instruments while he is performing the surgery.

Surgeons are still seeking a precise keratometer to assist them during operative procedures while providing minimal interference with those same operative procedures.

SUMMARY OF THE INVENTION

An object of the present invention is to provide an instrument that is capable of automatically providing an electro-optical measurement of corneal curvature in an operating room or clinical environment that eliminates the possibility of subjective or technical operator error.

Another object of the present invention is to provide an improved keratometer that is capable of being mounted on the exterior housing of an operating room microscope without requiring modification, retrofitting, or alteration of the microscope or its optical system.

Another object of the present invention is to provide an optical system for directly measuring a Purkinje image and which eliminates the need of incorporating any image doubling optical systems.

A further object of the present invention is to provide a keratometer that is capable of automatically permitting serial determinations of kerometric values at different meridians of observation. These measurements can be done automatically and can provide a continual and current output of kerometric values as a function of corneal meridian. Such an instrument is capable of providing measurements of corneal base curvature, steepest curvature, amount of astigmatism and axis of astigmatism.

An additional object of the present invention is to provide a visual display of the axis of steepest corneal curvature on the surface of the cornea visible to the surgeon.

The improved keratometer instrument of the present invention includes a housing member having means for direct attachment of the housing member to the exterior housing of the conventional operating room microscope. A ring light assembly provides a bright circular object that has a known geometric reference of a predetermined dimensional value on the cornea of the patient's eye. Electro-optical components can measure the image of the light ring and can produce electric signals representative of the desired measurements. These measurements can be automatically and continually made without any intervention by the surgeon and, if desired, the current status of the axis of astigmatism can be visually displayed to the surgeon viewing the patient's eye so he can make any adjustments in suture tension and wound closure and thereby minimize any undesired astigmatism induced by the operative procedures.

The features of the present invention which are believed to be novel are set forth with particularity in the appended claims. The present invention, both as to its organization and manner of operation, together with further objects and advantages thereof, may best be understood by reference of the following description taken in conjunction with the accompanying drawings.

DESCRIPTION OF THE PREFERRED EMBODIMENT

The following description is provided to enable any person skilled in the medical electro-optical field to make and use the invention and sets forth the best mode contemplated by the inventors in carrying out their invention. Various modifications, however, will remain readily apparent to those skilled in the art, since the generic principles of the invention have been defined herein specifically to provide a keratometer that can be readily manufactured and simply attached to an operating room microscope.

Figure 1:
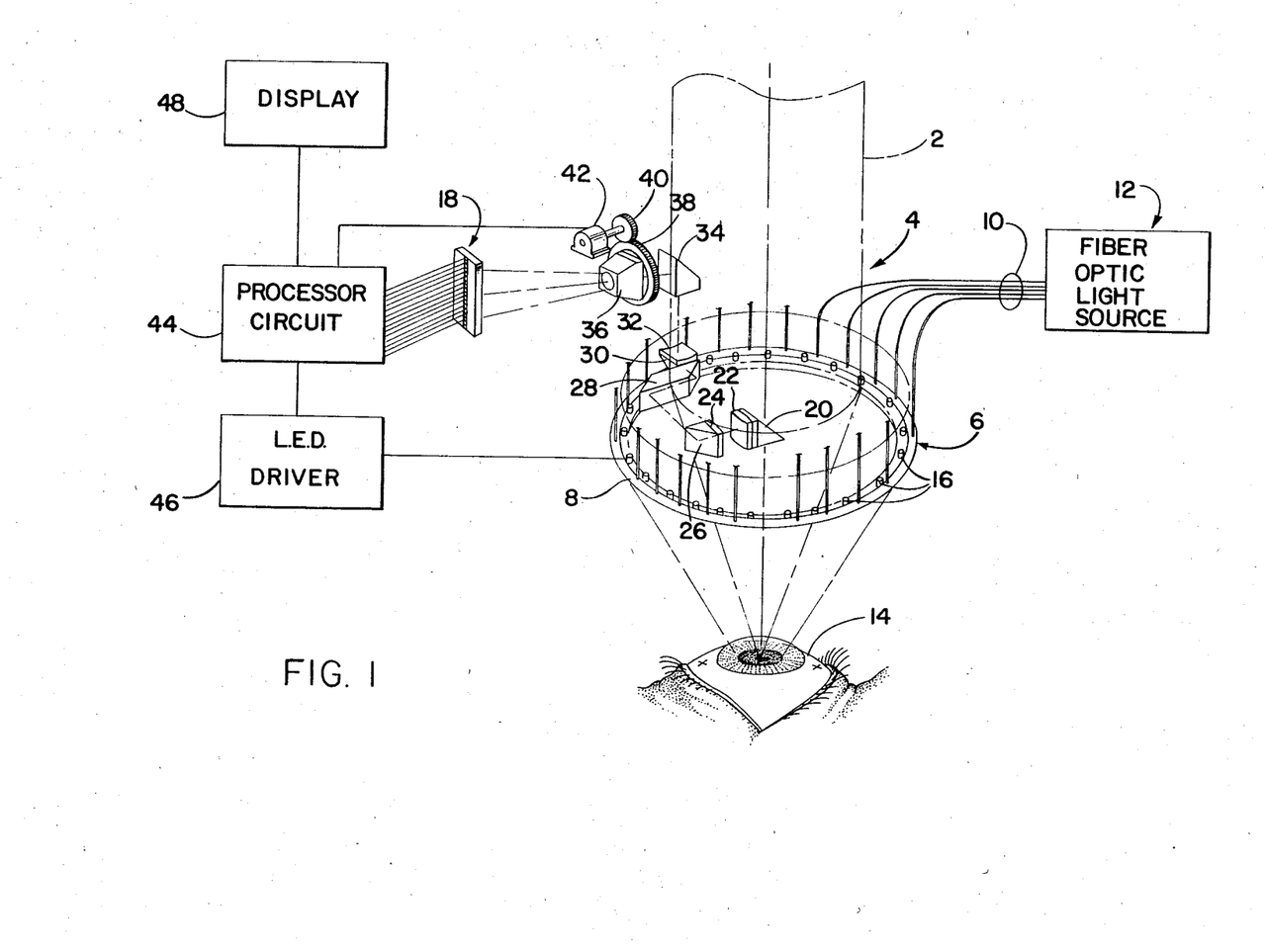
FIG. 1 is a schematic view of the present invention and its relationship to the cornea of a patient.

Referring to FIG. 1, a schematic perspective of the present invention is disclosed to assist the reader in understanding the principles and operation of the present invention. An operating room microscope such as the Carl Zeiss Model OpMi6S is schematically shown. This is a popular type of microscope that is used frequently in ophthalmic surgery. The keratometer instrument of the present invention includes an illuminated circular ring member 6 (more particularly shown in FIG. 2) that is positioned just below the plane of the entrance pupil of the operating microscope 2. The ring member 6 is positioned such that its center is coaxial with the center point of the entrance pupil of the operating microscope. The interface of mounting brackets (not shown) with the microscope 4 assures this positioning so that any reference light produced by the ring member will be centered on the cornea if the operating microscope 2 is centered on the cornea. The ring member 6 includes an acrylic rod of roughly ⅛ inch in diameter which acts as a diffusion lens 8 and is interconnected with either a plurality of small light sources or a plurality of individual fiber optic members 10 that are in turn connected to a standard projection type light source inside a remote light source housing assembly 12. These fiber optic members 10 travel from their origination at the light source housing assembly 12 to a point adjacent the light ring member 6. They then fan out to enter into the circumferance of the ring member 6 at radially spaced points. Activation of the light source will thereby uniformly illuminate the entire ring to provide a discrete circulate mire image that can be projected on the cornea of the patient's eye such as shown in FIG. 1.

Equally spaced about the circumferance of the light ring 6 are a plurality of light emitting diodes 16 (LED) that can be individually activated, for example 36 or 72 light emitting diodes can be equally spaced at 10° or 5° radial positions adjacent to the light ring 6. The purpose of these light emitting diodes 16 will be subsequently explained.

The optical imaging system of the present invention will now be described. As traced along a folded optical path, from the cornea of the patient's eye 14 to a photodetective array such as a Fairchild Model No. CCD133DC charge coupled device (CCD) 18, the following optical elements provide an image of the geometric reference Purkinje image that is realized by the projection of the diffusion lens 8 on the cornea. A right angle prism 20 (FIGS. 1 and 2) receives the Purkinje image and has mounted on its exit face an achromat doublet 22. The image transmitted from the doublet 22 contacts a plano-convex positive lens 24 mounted on a second right angle prism 26. The optical path is again folded to contact a rhomboid prism 28 that is appropriately bonded to a right angle prism 30 having a plano-meniscus negative lens 32 bonded to its exiting face. Finally, another right angle prism 34 again folds the light path to enter into a pechan prism 36. The surfaces of the optical elements are coated with an antireflective coating as known in the prior art. In summary, this optical system incorporates a series of reflecting surfaces to fold the optical axis and a lens group to realize the Purkinje image of the light ring 6 eventually on the photoelectric detector array 18. The pechan prism 36 provides an automatic image rotation as will be subsequently described.

The entrance prism 20 is located just below the plane of the entrance pupil of the microscope within the illuminating ring 6, see FIG. 2. The combination of these optical components is designed to view the cornea from a point midway between the respective entrance pupils of the binocular eye pieces of the operating microscope. In this manner, the field of view of the keratometric optic system is coaxial with the view of the operating microscope. The optics project the image of the ring lamp image to focus at the plane of the photoelectric array. Because the eye is essentially passive during the brief time a sample is taken (e.g., during surgery, the eye is in deep anesthesia and relatively free of muscle tremor or saccades), the image will be sufficiently stable to ensure reliable measurements. As will be described, some of the optical elements can be mounted on a moveable glass platform such that, when properly positioned for measurement, they may intrude slightly into the field of view of the microscope. If desired, this platform can be removably mounted to retract these elements from the field of view of the microscope and thus allow an unobstructed view through the microscope.

Figure 2:
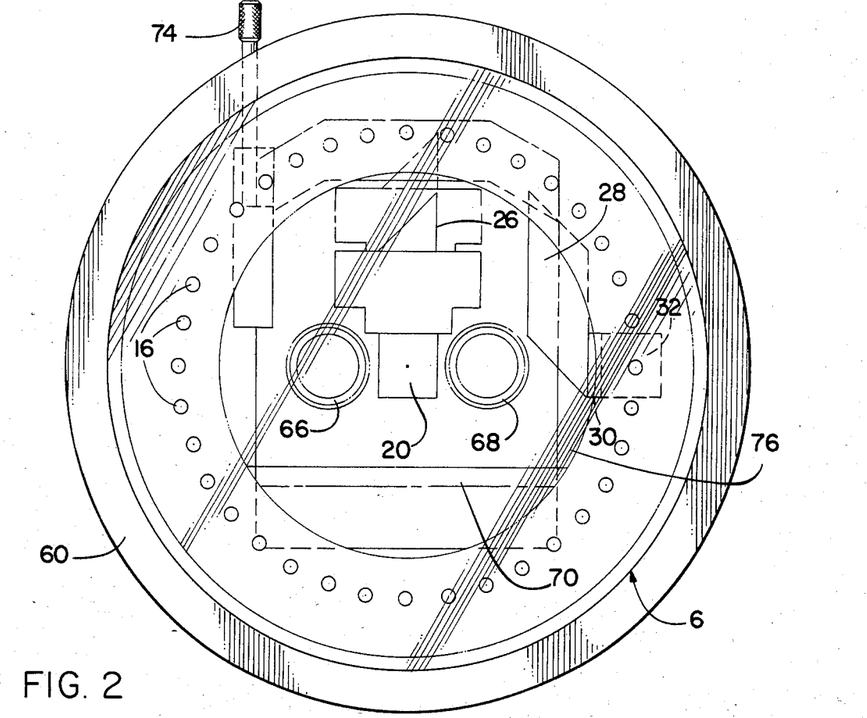
FIG. 2 is a bottom view of the portion of the present invention mounted on the bottom surface of the microscope which shows the pupil-sharing feature of the microscope and keratoscope.
Figure 5:
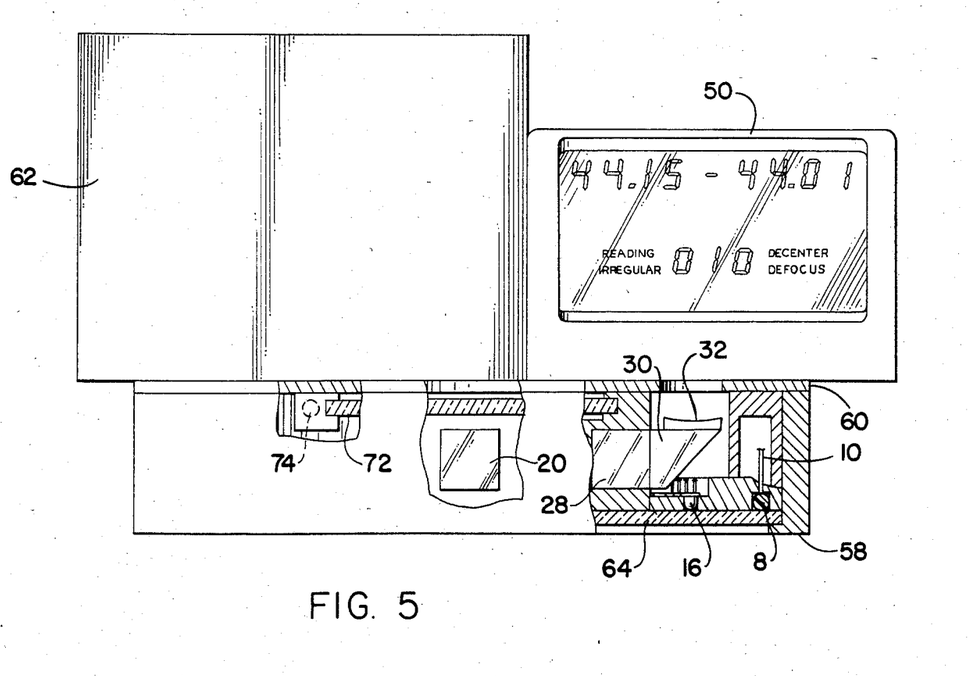
FIG. 5 is a partial schematic side view of the present invention.

Referring to FIG. 5, a housing member 58 is attached by a circular mounting plate 60 disclosed in FIG. 2 to the microscope 2. The upper portion of the housing member 58 can support respectively a cover member 62 for the stepper motor 42, array 18, electronic hardware, etc. Additionally the display 50 for the operator can also be supported above the housing member 58. Enclosing the bottom surface of the housing member 58 is a glass plate 64 that respectively supports the diffusion rod 8 of the light ring 6 and the radially spaced LED indicators 16. On the inside of the glass plate 64 adjacent the rod 8 is a Stewart film screen to provide high gain diffusion. A glass plate 72 is capable of mounting a portion of the optical elements that transmit the reflected image from the eye to the array 18 and this glass plate 72 is positioned just below the entrance pupil of the microscope. The glass plate 72 which supports, for example, the entrance prism 20, is movably mounted and can be adjusted for lateral movement by a spindle member 74.

As can be seen in FIG. 2, the entrance prism 20 is positioned between the left eye pupil 66 and the right eye pupil 68 of the microscope. The respective eye pupils share a common entrance lens 76 that is appropriately segmented along one edge to accommodate a light source 70 for illuminating the patient's eye during an operation.

The pechan prism 36 is rotatably mounted to permit rotation of the prism about its axis, and to produce a corresponding rotation of the ring lamp image on the photoelectric array 18. As can be appreciated a scanning relative translation of the image and the array 18 can also be used with appropriate adjustments in an alternative embodiment of the invention. A ring gear 38 can be driven by a pinion gear 40 that is attached to the output shaft of a stepping motor 42. As can be appreciated, the gear arrangement can be more complex for transmission of the rotation of the stepping motor 42 and to prevent any backlash of the gears. Holes in the gear (not shown) can be used with a LED photodetector pair to provide an optical position sensor 52 for determining the orientation of the Purkinje image on the array.

Figure 4:
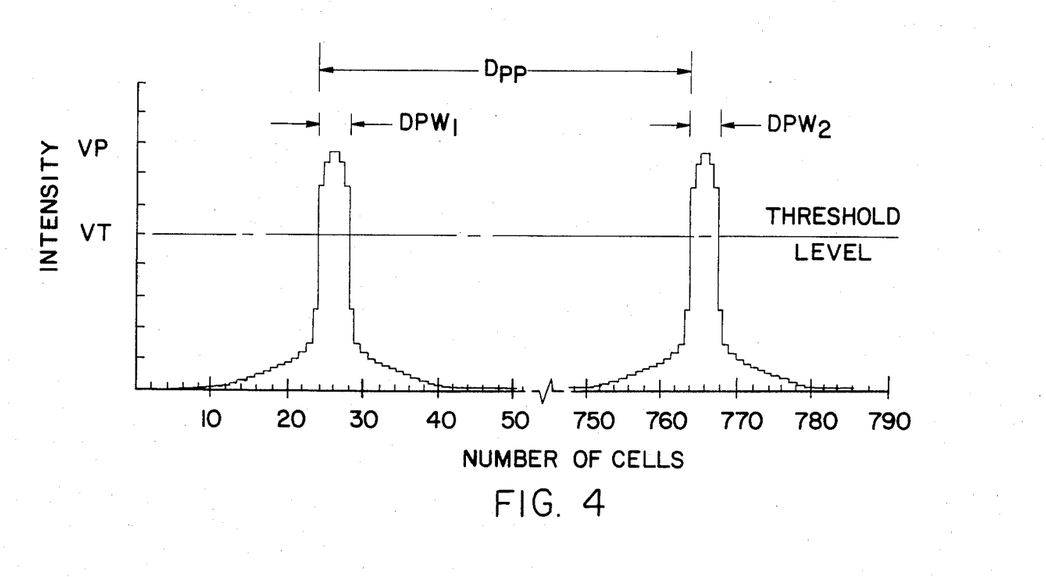
FIG. 4 is a schematic diagram of the output of the CCD array with an image focused thereon.

The realization of the ring image on the photoelectric array 18 will illuminate two regions of the array 18 as can be seen in FIG. 4. The array 18 can be serially "read out" electronically and the number of detector cells between the two illuminating regions provides a precise measurement of the image size produced by the corneal reflection. The rotation of the pechan prism 36 correspondingly rotates the image of the ring and accordingly, permits a corneal curvature measurement at several meridians and a determination of the axis of orientation of the steepest curvature of the eye surface.

Figure 3:
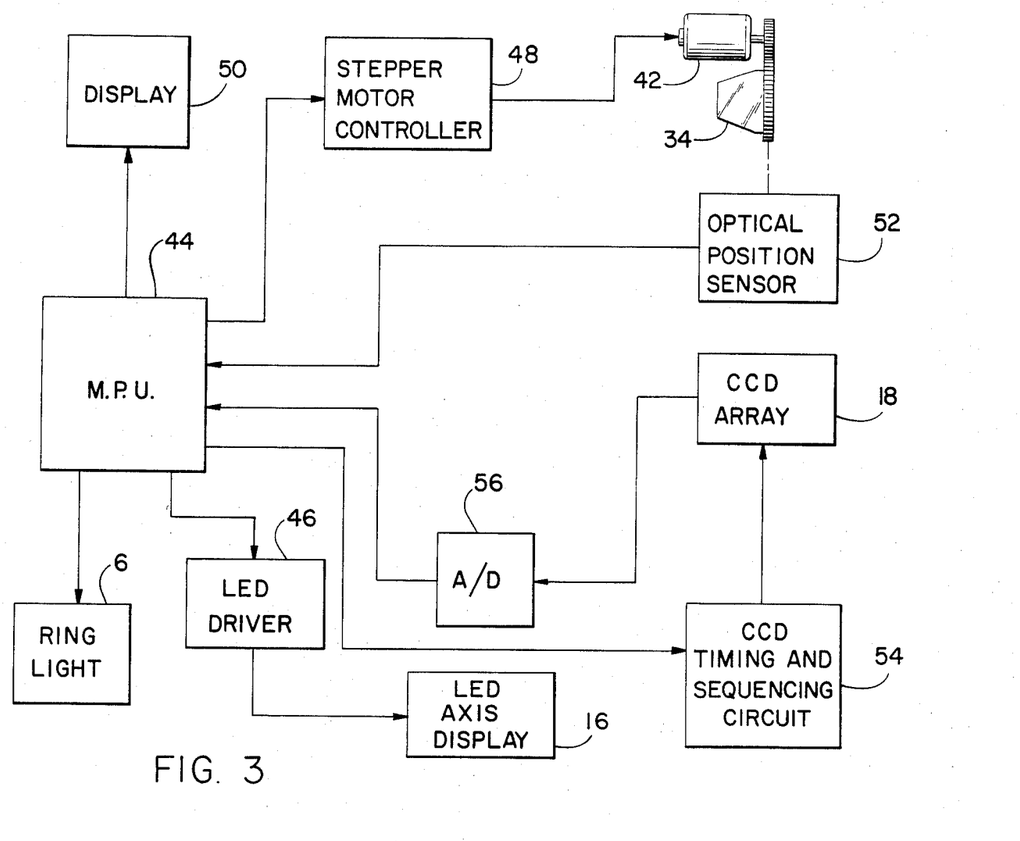
FIG. 3 is a schematic diagram of the major elements of the present invention.

Referring to FIG. 3, the stepper motor 42, such as a Rapidsyn Model No. 11R-01X can be controlled by a microprocessor 44 such as an Intel 8080 to automatically and precisely step the pechan prism 36 to permit a serial reading of keratometric values at different meridians of observation. The display 50 and/or the LED driver circuit 46 and LED's 16 can provide information to the surgeon on the axis of astigmatism. By determining the axis of astigmatism the surgeon can either control or modify the corneal astigmatism by adjusting the tension of the suture. Recently, it has been found in ophthalmic surgery that a predisposition of astigmatism, that is, an intentional introduction of astigmatism in anticipation of the postopereature relaxation of the wound, can eliminate an undesired astigmatism which can be generated upon healing of the wound.

The microprocessor 44 can control a stepper motor controller 48 such as a Rapidsyn Model No. DCP-23, that is particularly adapted to drive the stepper motor 42. An optical position sensor 52 can provide information to the microprocessor 44 that permits a determination of the orientation of the image.

As can be readily appreciated, the stepper motor 42 can be initially driven to a null position as monitored by the optical position sensor 52. The stepper motor controller 48 can appropriately step the stepper motor 42 for rotation of the pechan prism 34. For example, the prism 34 can be made to rotate in increments of 5° or 10° or any predetermined increment that is desired. The microprocessor circuit will then activate a CCD timing and sequence circuit 54 such as a Fairchild Model No. CCD 133DB for sequentially polling the CCD array after each increment to provide a signal representative of the measured peak-to-peak signals as shown in FIG. 4. An analog digital converter 56 will digitize this information and provide it to an appropriate register in the microprocessor 44 for subsequent storage. With this information the microprocessor 44 can compute a corneal curvature measurement at each meridian and also determine the axis of orientation of the steepest curve of the eye surface. As should be appreciated, it is also capable of calculating an intraocular lens power and also displaying this on a display 50 to the operator.

An operator display 50 is capable of providing alphanumerical information, for example, with conventional LED elements resulting from computation by the microprocessor circuit 44 as shall be described herein.

Figure 6:
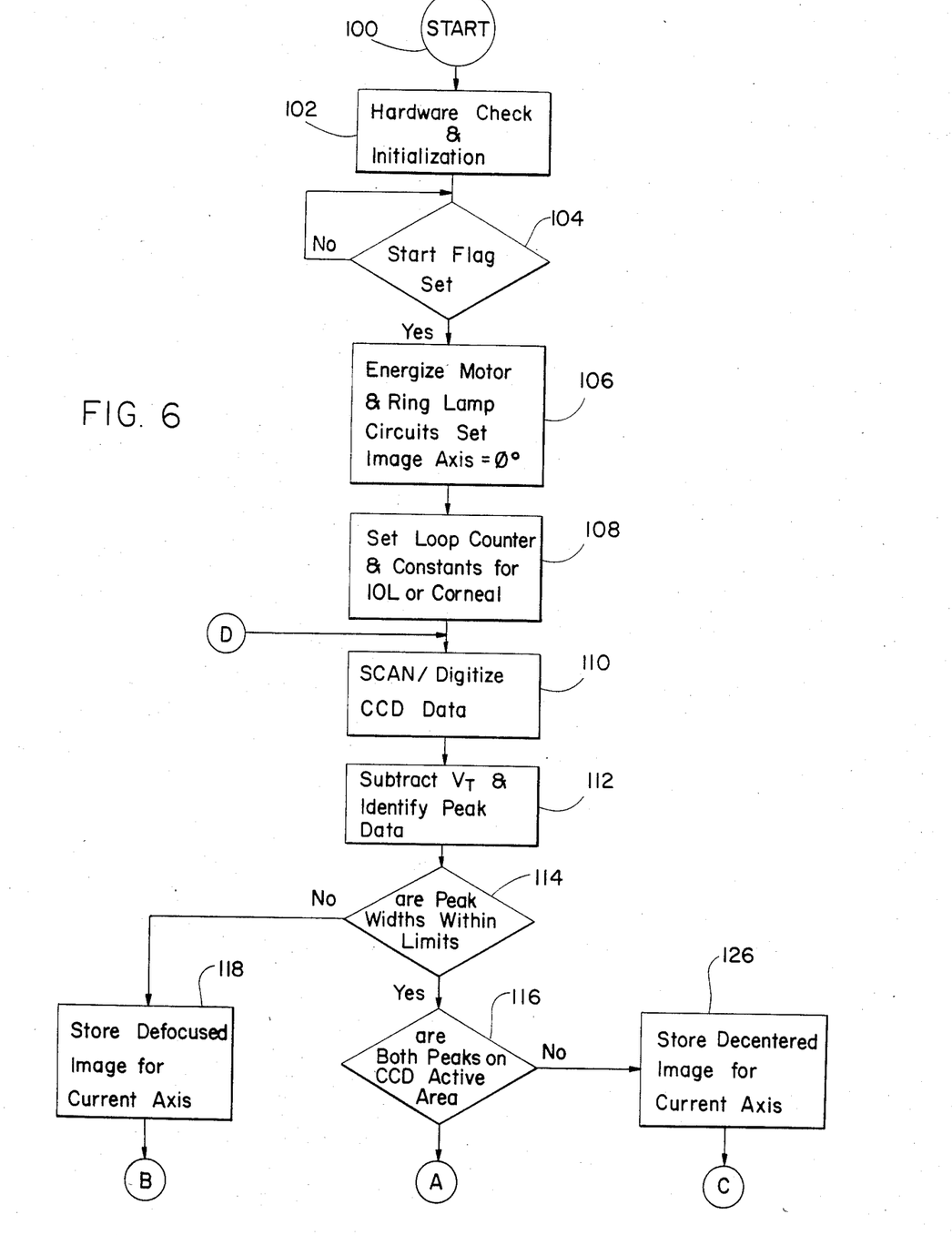
FIGS. 6 and 7 are flow charts of the control program.
Figure 7:
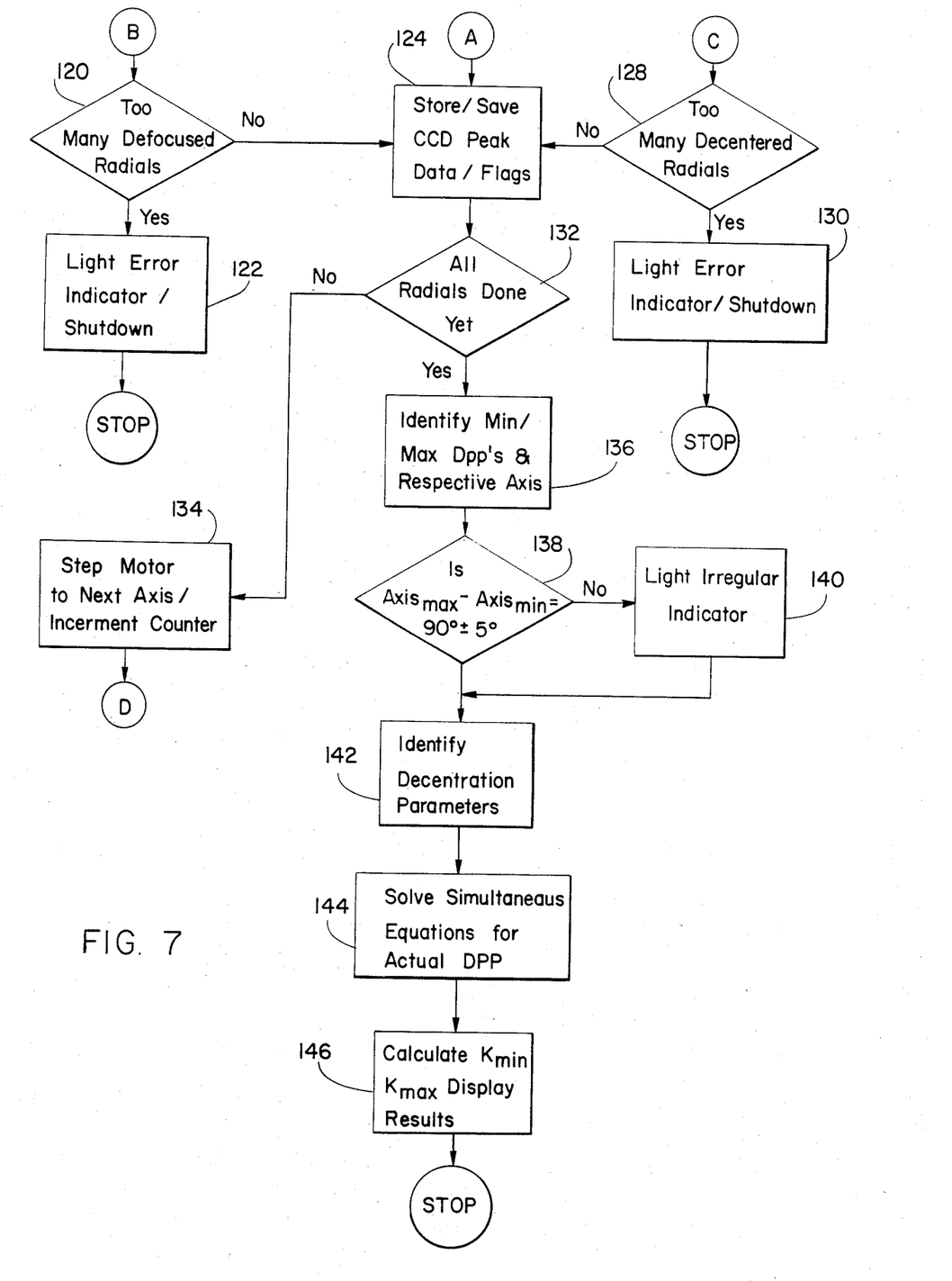

Referring to FIGS. 6 and 7, a flow chart of the basic program, simplified for purposes of illustration, is provided. Activation of a start switch 100 will implement a subroutine 102 to check on the operability of the system hardware and whether the power supply is at an adequate level. During the initialization, the display LED's are blanked on the display 50 and also the LED elements on the LED axis display 16 are blanked. The voltage setting on the light source power supply 12 is confirmed as being set at high and all entries previously stored in the buffer memory of the microprocessor 44 are dumped. When the operator decides to initiate a measurement, an appropriate start flag is set and checked at step 104. If the answer is "yes" the program proceeds to step 106 wherein the stepper motor 42 is energized. If the pechan prism 34 is not properly positioned at 0° then the stepper motor 42 is activated to drive the prism 34 to a 0° position as monitored by the optical position sensor 52.

At step 108 a counter is set for determining a measurement at each meridian, and various predetermined constants are retrieved from storage depending upon whether or not a cornea keratometry measurement or an IOL power measurement is desired. At step 110, measurements are fed from the CCD array 18 via the analog to digital converter 56 into the microprocessor unit 44 upon initiation of the timing and sequencing circuit 54. With reference to FIG. 4, the threshold voltage, VT, is subtracted in step 112 to determine those elements of the CCD array or cells (e.g., out of a total of 1028 cells) that are responsive to the illumination of the projected ring image. The resulting peaks are detected and calculated to determine a peak-to-peak distance and if the peak widths, $DPW_1$ and $DPW_2$ are within predetermined limits as set forth in step 114 the measurement cycle continues. If, however, the peaks are not within certain limits, e.g., greater than 5 cells, then a defocus condition is recorded in step 118 and in step 120 a decision is made as to whether too many defocused readings have been recorded, e.g., 15 sequential reading indicating defocusing. If the answer is "yes," then a defocused light indicator is lit as an error and the program measurement cycle is shut down in step 122. If there have not been too many defocused readings or if the readings have been within the predetermined limits, then the data is stored and saved in a retrievable memory in step 124. If two separate peak signals are not measured then a decentered image is recognized in step 126, and if too many decentered images based upon a predetermined limit, e.g., 10 sequential readings, are encountered in step 128, then a decentered light error indicator is activated and the measurement cycle is shut down in step 130. A counter (not shown) is polled in step 132 and if all the radial measurements have been accomplished, then the program continues on to perform the desired keratometry calculations. If all the radial measurements have not been accomplished, then in step 134 the program is looped back between steps 108 and 110 and the stepper motor 42 is activated for another incremental movement, the counter being incremented.

In incrementing the program through step 132 it should be recognized that the prism stepper motor 42 rotates the images of the ring light on the CCD array by a preset number of degrees such as 5° for all meridians from 0° to 180°. A sufficient timing pause is permitted to allow the prism 34 rotation to occur. The prism position can be stored in a buffer or can be incremented with a counter for either counting up or counting down to a preset number of meridian steps. The actual measurement counts the number of cells between the peaks and multiplies by the individual cell width to derive the actual peak-to-peak distance (Dpp). The Dpp measurement electronically represents the measured image diameter of the illumination ring. The measurement is then stored in a RAM memory (not shown) with the address coded to the particular meridian axis.

In step 136 the program searches the memory to find the maximum and minimum values of peak-to-peak distances (Dpp) and their corresponding axes.

In step 138 a calculation is performed by the program to determine if the maximum axis is 90°±5° greater than the minimum axis. If it is not, then an indicator is provided to the operator, for example, by lighting a signal light in step 140 to indicate an irregular astigmatism condition. If the value is found to be within these parameters in step 138 then the program proceeds to step 142 to identify decentration parameters, if any. In step 144 the keratometry equations to be described subsequently are solved for the actual peak-to-peak distance, Dpp, measurements and in step 146 the minimum and maximum K values and the axis of steepest curvature are calculated and are displayed, and appropriate LED's are illuminated to visually display the steepest curvature axis on the cornea.

In calculating the corneal keratometry, a subroutine of the program deals with a conversion of the measured image diamter Dpp, seen by the CCD array 18 into a calculated numerical value of corneal curvature in diopters (K value). This algorithm provides accurate K values in the event that the ring lamp image is not precisely centered on the CCD centerline by a coordinate transformation method. Because the CCD centroid and the centroid of the ring lamp image will not generally be coincident, a coordinate transformation algorithm is used to calculate the true maximum and minimum corneal curvatures. Since the ring lamp image will be a smooth continuous convex curve with no predictable geometry or symmetry, a method which assumes a general closed curve is used.

The principal of any keratometer is that an object of known size (in this case, the diameter of the illuminating ring 8), when placed in front of a curved reflecting surface (the cornea), will form a reflected image. On a first-order basis, the size of this image is directly proportional to the radius of curvature of the reflecting surface. The general keratometric equation is as follows:

$$r = (2h'd)/h \qquad (1)$$

where r is the radius of curvature, h' (DPP) is the image size, d is distance from object to reflecting surface, and h is object size. To convert the radius of curvature to a dioptric power, one employs another standard optical formula:

$$D = (n_1 - n_2)/r \qquad (2)$$

where D is dioptric power, $n_1$ the refractive index of the cornea (1.3375), and $n_2$ the refractive index of air (1.00). Therefore, $$D = 0.3375/r \tag{3}$$

Substituting (3) into (1), and solving for D, we have:

$$\begin{aligned} D &= (0.3775h)/2h'd) \\ &= (0.1687h)/(h'd) \end{aligned} \tag{4}$$

Thus, D can be calculated if h and d are constant, and h' can be measured. The value h is fixed, being the diameter of the illumination ring, and d, the ring-light to cornea distance, is known because the ring is fixed to the operating microscope, the scope has a fixed focal length. If the ring-light is located at the plane of the microscope objective lens, then d equals the objective lens focal length.

Generally h will be 12.0 cm, and d will be 17.5 cm (175 mm focal length). The CCD array is able to measure the value h' thereby providing all necessary data to calculate D. These values can change depending on the particular microscope and appropriate adjustments would be necessary to compensate or calibrate correct values into our program.

Substituting the anticipated values for d (17.5 mm) and h (12 cm) into equation (4) above, we have $$\begin{aligned} D &= ((0.1687)(0.12))/((0.175)h') \\ &= 0.1157148/h' \end{aligned} \tag{5}$$

Using equation 5 above, it is possible to convert the measured image diameter h' (DPP) to a keratometry value for display to the operator.

As mentioned earlier, a particular advantage of the present invention is the ability to provide the current axis of astigmatism to the surgeon in a manner that is superimposed with the surgeon's view of the patient's eye so that he can minimize any undesired astigmatism by suture adjustment. This is accomplished by activating two diametrically opposed LED elements adjacent the reference ring light so that the surgeon can actually see a reflection of the LED elements. The LED elements can either be of a different color or can blink, e.g., at 2 Hz, to distinguish the axis from the ring light. In implementing this feature, a subroutine can search and recall from memory the axis of the K max. From this information the appropriate LED elements can be illuminated. If the axis is located on the meridian of a pair of LED elements then only those elements will be lit. If the axis is located between adjacent LED elements then two pair of LED elements located 180° apart will be lit to indicate a meridian between adjacent LED elements. Of course the K max value can also be displayed as a numerical value on the display 50. While not disclosed herein, it would also be possible to display a predetermined desired axis as a guide. For example, a pair of LED elements could blink at the desired axis and the surgeon could adjust the suture tension to match the measured axis (constantly lit) with the desired (blinking) axis.

The keratometer 4 of the present invention is also capable of calculating the intraocular lens (IOL) power and displaying the same to the operator, since this value directly effects the restored vision of a patient it is prudent for an implanting surgeon to check the manufacturer's labeled power prior to implantation. Essentially this subroutine can be performed in a similar fashion to the subroutine for calculating the corneal keratometry, with two important differences.

First, the index of refraction of methyl methacrylate plastic, used in the manufacture of intraocular lenses, is different from that of the cornea; this must be taken into account when processing the data. The second difference relates to data sampling frequency, since IOL manufacture and quality control techniques already exist to minimize IOL astigmatism, this is not a major problem that needs to be dealt with by a surgical keratometer. However, the ability of an operative keratometer to measure spherical power of an IOL is quite important, as it provides the only safeguard against accidental insertion of the wrong IOL at surgery (i.e., one of incorrect power for the eye in question). Thus, it is not necessary to sample IOL power every 5° as in the measurement of corneal power, sampling at 30° intervals is adequate.

IOL power is calculated with the same equations described in the above subroutine for calculating corneal keratometry, but the refractive index of IOL plastic is substituted for that of the cornea. This value is 1.490. This allows the measured image diameter to be converted to IOL power, when equations (2) through (5) above and equations (6) through (8) below are utilized appropriately. The value for IOL power at a given axis is then stored in a buffer memory.

The refractive index of the corneal substance is 1.376 when measured in air. The refractive index of precorneal tear film is 1.336. Since the rear surface of the cornea is in contact with aqueous humor (n=1.336 also), the refractive contribution of the rear surface is very small; however, it is not insignificant. Most commercial keratometers utilize a fictitious refractive index of n=1.3375 to correct for the teak film interface, and rear surface corneal power. This value has been used in the above equations and calculations as well.

The refractive index of polymethyl methacrylate is 1.490. Since IOL's are bathed on both front and rear surfaces by aqueous humor (n=1.336), the effective refacting power of the lens is reduced from what it would be in air. With the keratometer, however, we are attempting to measure the lens in air, and determine its computed refracting power in aqueous. For this purpose, a correction factor must be introduced. For lens power in air, $$\begin{aligned} D_{air} &= (n_{lens} - n_{air})/r \\ &= (1.490 - 1.000)/r \\ &= 0490/r \end{aligned} \tag{6}$$

Solving for r, we have $r = 0.490/D_{air}$. Similarly, for lens power in aqueous, $$\begin{aligned} D_{aqu} &= (n_{lens} - n_{aqu})/r \\ &= (1.490 - 1.336)/r \\ &= 0.154/r \end{aligned} \tag{7}$$

Now, to measure IOL power in air, and convert to power in aaqueous, we substitute (6) and (7), as follows:

$$\begin{aligned} D_{aqu} &= (.154/.490) D_{air} \\ &= 0.314 \, D_{air} \end{aligned} \tag{8}$$

Thus, IOL power in aqueous can be determined by measuring the power in air using $n_{lens} = 1.490$, and multiplyiung the result by 0.314.

Thus the present invention provides a keratometer that can automatically and continually provide objective keratometric values to an observer with a minimum demand on his attention. The steepest curvature of the eye surface can be displayed directly on the eye so that the surgeon can adjust his surgical technique accordingly.

Other modifications of the present invention are possible are accordingly the scope of the present invention should be limited by the specific embodiment disclosed herein and should be measured solely from the following claims wherein we claim.

What is claimed is:

1. A keratometer instrument capable of measuring keratometric values of an eye comprising:
   means for creating a radiating object source of a known dimension for reflection of only one Purkinje image from the surface of an eye;
   photoelectric means for receiving the reflected image and converting it into electrical signals indicative of the size of the image;
   means for determining from the electrical signals if the image is in focus and providing an enabling signal when in focus; and
   means for generating keratometric values from the electrical signals of image size when the enabling signal indicates an in focus condition, whereby the operator is not required to adjust the instrument and has constant and current keratometric values available.

2. The invention of claim 1 further including means for taking discrete predetermined measurements at different meridians of the eye surface and means for displaying the axis of orientation of the steepest curvature of the eye surface.

3. The invention of claim 1 wherein the means for creating a radiating object includes a diffusion lens, a source of light and a plurality of fiber optic elements, the fiber optic elements interconnecting the diffusion lens with the source of light.

4. The invention of claim 1 wherein the photoelectric means for receiving the reflected image includes a plurality of prisms and a telephoto objective lens group, the prism folding the optical axis between lens elements of the telephoto objective.

5. The invention of claim 4 wherein one of the prisms is rotatably mounted for rotation of the Purkinje image.

6. The invention of claim 4 wherein a linear photo conductive array is operatively positioned to receive the image of the telephoto objective lens group.

7. The invention of claim 2 wherein the means for displaying the axis of orientation of the curvature of the eye surface includes a plurality of light emitting elements that can be selectively activated to indicate an axis directly on the eye surface.

8. The invention of claim 5 further including a steeper motor connected to the rotatable prism for positioning the prism at discrete predetermined positions to take measurements at different meridians of the eye surface.

9. The invention of claim 1 further including means for mounting the instrument on a binocular microscope having an entrance pupil plane.

10. The invention of claim 9 wherein the means for receiving the reflected Purkinje image includes an optical element positioned approximately in the entrance pupil plane of the microscope and between the respective left and right entrance pupils of the microscope.

11. The invention of claim 1 further including compensation means for adjusting the measured signals representative of the size of the image to compensate for a decentered image relative to the receiving means.

12. An improved keratometer instrument capable of measuring keratometric values of an eye during surgery comprising:
    means for providing a reference of a predetermined dimensional value to the cornea of the eye:
    photoelectric means for receiving the reflected image of the reference and converting it into electrical signals indicative of the size of the reference;
    means for determing a defocused condition of the image and providing a corresponding defocus signal to the user, and
    means for automatically determining from the electrical signals the keratometric values, if a defocus signal is not generated, whereby the operator is not required to adjust the instrument and has constant and current keratometric values available.

13. The invention of claim 12 further including compensation means for adjusting the measured signals representative of the size of the image to compensate for a decentered image on the photoelectric means.

14. The invention of claim 12 further including means for displaying the steepest curvature of the eye surface including a plurality of light emitting elements that can be selectively activated to indicate an axis of orientation directly on the eye surface.

15. The invention of claim 12 further including the means for automatically rotating the image which includes a prism and a steeper motor connected to the rotatable prism for positioning the prism at discrete predetermined positions to take measurements at differenct meridians of the eye surface.

16. The invention of claim 15 wherein the means for receiving an image includes a linear photo detective array that is operatively positioned to receive the image.

* * * * *

UNITED STATES PATENT OFFICE
CERTIFICATE OF CORRECTION

Patent No. 4,597,648     Dated July 1, 1986

Inventor(s) David Wallace et al.

It is certified that error appears in the above-identified patent and that said Letters Patent are hereby corrected as shown below:

Column 9, Equation (4)
"(0.3775h)" should be --(0.3375h)--.

Column 12, line 49-50
"differenct" should be --different--.

Signed and Sealed this

Eleventh Day of November, 1986

Attest:

DONALD J. QUIGG

Attesting Officer     Commissioner of Patents and Trademarks